US007974860B1

(12) United States Patent
Travis

(10) Patent No.: US 7,974,860 B1
(45) Date of Patent: Jul. 5, 2011

(54) CONSUMER DIRECTED HEALTH PLAN (CDHP) AND HIGH DEDUCTIBLE HEALTH PLAN (HDHP) COUNSELING AND INFORMATION DISTRIBUTION

(75) Inventor: Roger M. Travis, Bozeman, MT (US)

(73) Assignee: ExperienceLab, Inc., Bozeman, MT (US)

( * ) Notice: Subject to any disclaimer, the term of this patent is extended or adjusted under 35 U.S.C. 154(b) by 318 days.

(21) Appl. No.: 12/118,313

(22) Filed: May 9, 2008

(51) Int. Cl.
*G06Q 40/00* (2006.01)
(52) U.S. Cl. ......................................... 705/4
(58) Field of Classification Search .................. 705/4
See application file for complete search history.

(56) References Cited

U.S. PATENT DOCUMENTS

| 6,208,974 | B1 | | 3/2001 | Campbell et al. ................ 705/3 |
| 6,658,391 | B1 | * | 12/2003 | Williams et al. ................ 705/10 |
| 7,077,806 | B2 | * | 7/2006 | Ackermann et al. .......... 600/300 |
| 7,707,087 | B1 | * | 4/2010 | Rogers et al. .................... 705/35 |
| RE41,493 | E | * | 8/2010 | Marcus .......................... 707/740 |
| 2002/0059587 | A1 | | 5/2002 | Cofano et al. .................... 725/35 |
| 2002/0147617 | A1 | | 10/2002 | Schoenbaum et al. ............ 705/4 |
| 2003/0009367 | A1 | * | 1/2003 | Morrison .......................... 705/9 |
| 2004/0024620 | A1 | * | 2/2004 | Robertson et al. ................ 705/4 |
| 2004/0210661 | A1 | * | 10/2004 | Thompson ..................... 709/228 |
| 2004/0234065 | A1 | | 11/2004 | Anderson ............... 379/266.07 |
| 2007/0250349 | A1 | * | 10/2007 | Tieger .............................. 705/3 |
| 2008/0082351 | A1 | * | 4/2008 | Kelley-Hrabe et al. .......... 705/1 |
| 2008/0167891 | A1 | * | 7/2008 | Cohn et al. ....................... 705/1 |

OTHER PUBLICATIONS

Non-Final Office Action in U.S. Appl. No. 11/928,511 mailed Aug. 6, 2010, 11 pages.

* cited by examiner

*Primary Examiner* — James Kramer
*Assistant Examiner* — Eric T Wong
(74) *Attorney, Agent, or Firm* — Fish & Richardson P.C.

(57) ABSTRACT

Methods and systems for directing enrollment and/or use of health and wellness plans based on personality type are disclosed.

12 Claims, 8 Drawing Sheets

US 7,974,860 B1

CONSUMER DIRECTED HEALTH PLAN (CDHP) AND HIGH DEDUCTIBLE HEALTH PLAN (HDHP) COUNSELING AND INFORMATION DISTRIBUTION

TECHNICAL FIELD

The invention relates to using personalities to direct enrollment and/or use of health care plans, wellness plans, and/or other health-related initiatives.

BACKGROUND

Companies often offer various health related services to their employees. Depending on the type of service and the cost of the service to the employer and/or employee, an employer may desire to encourage or discourage enrollment in particular types of health related services. Examples of health related services provided by an employer include, health insurance plans such as consumer directed health plan, high deductible health plans, and other insurance plans; wellness programs; and/or other health and wellness related services. In general, a consumer directed health plan engages consumers more directly in their health care purchases. Consumer directed health plans often make cost and quality information evident to the consumer (e.g., through the Internet) with the goal of creating a more efficient health care market. High deductible health plan health insurance plans often offer lower premiums and higher deductibles than a traditional health plans. HDHP health insurance plans are sometimes referred to as a catastrophic health insurance plan.

SUMMARY

In some aspects, a method for distributing information about health related plans or programs can include distributing information based on a predicted personality trait for the individual.

In some aspects, a method can include predicting, in response to a computer automated survey, a personality trait for an individual. The method can also include receiving information related to the usage of a consumer directed health plan or high deductible health plan by the individual. The method can also include providing, based on the predicted personality trait for the individual and the information related to the usage, information about use of the consumer directed health plan or high deductible health plan to the individual, the information being different for different individuals having different predicted personality traits.

Embodiments can include one or more of the following.

The information about use of the consumer directed health plan or high deductible health plan can include information related to reducing costs to the individual for medical services. The information about use of the consumer directed health plan or high deductible health plan can include information related to preventative healthcare. The information about use of the consumer directed health plan or high deductible health plan can include information related to locating a health care provider. The predicted personality trait can be based on at least one of spending attitudes of the individual and attitudes of the individual toward medical treatment. Predicting the personality trait for the individual can include predicting the personality trait for the individual based on at least one of past interaction information, demographic data, questionnaire answers, and credit bureau data. The computer automated survey can include 30 questions or fewer (e.g., 30 questions or fewer, 25 questions or fewer, 20 questions or fewer, 10 questions or fewer).

In some aspects, a method can include receiving responses to a survey from a user and receiving profile information about the user. The method can also include determining a particular personality group of a plurality of personality groups to associate with the individual based on the received responses and profile information and enrolling the user in a consumer directed health plan or high deductible health plan. The method can also include using the determined particular personality group to provide information to the user subsequent to the user's enrollment in the consumer directed health plan or high deductible health plan, the information being tailored based on the particular personality group associated with the individual.

Embodiments can include one or more of the following.

The method can include using the determined particular personality group to increase enrollment in the consumer directed health plan or the high deductible health plan. The method can include prior to enrollment of the user in the consumer directed health plan or high deductible health plan, providing information to the user about the consumer directed health plan or the high deductible health plan based on the determined particular personality group.

In some aspects, a method for presenting information about a health plan to an individual includes determining information about usage of a consumer directed health care plan to present to an individual enrolled in the consumer directed health care plan based on a predicted personality trait for an individual. The method also includes providing a first call script to be used by a consumer directed health care plan support agent for individuals with a first personality type. The method also includes providing a second call script to be used by the consumer directed health care plan support agent for individuals with a second personality type, the first call script being different from the second call script. The method also includes determining a particular one of the first and second call scripts based on the predicted personality trait of the individual.

Embodiments can include one or more of the following.

The predicted personality trait can be based on how the individual will respond to various types of information about health care options. The method can also include predicting the personality trait for the individual based on at least one of past interaction information, demographic data, questionnaire answers, and credit bureau data. The personality type can include at least one of expert seeking, confident, loyalist, advice seeking, challenged, dependent, and indifferent.

Other features and advantages of the invention will become apparent from the following description, and from the claims.

DESCRIPTION

Figure 1:
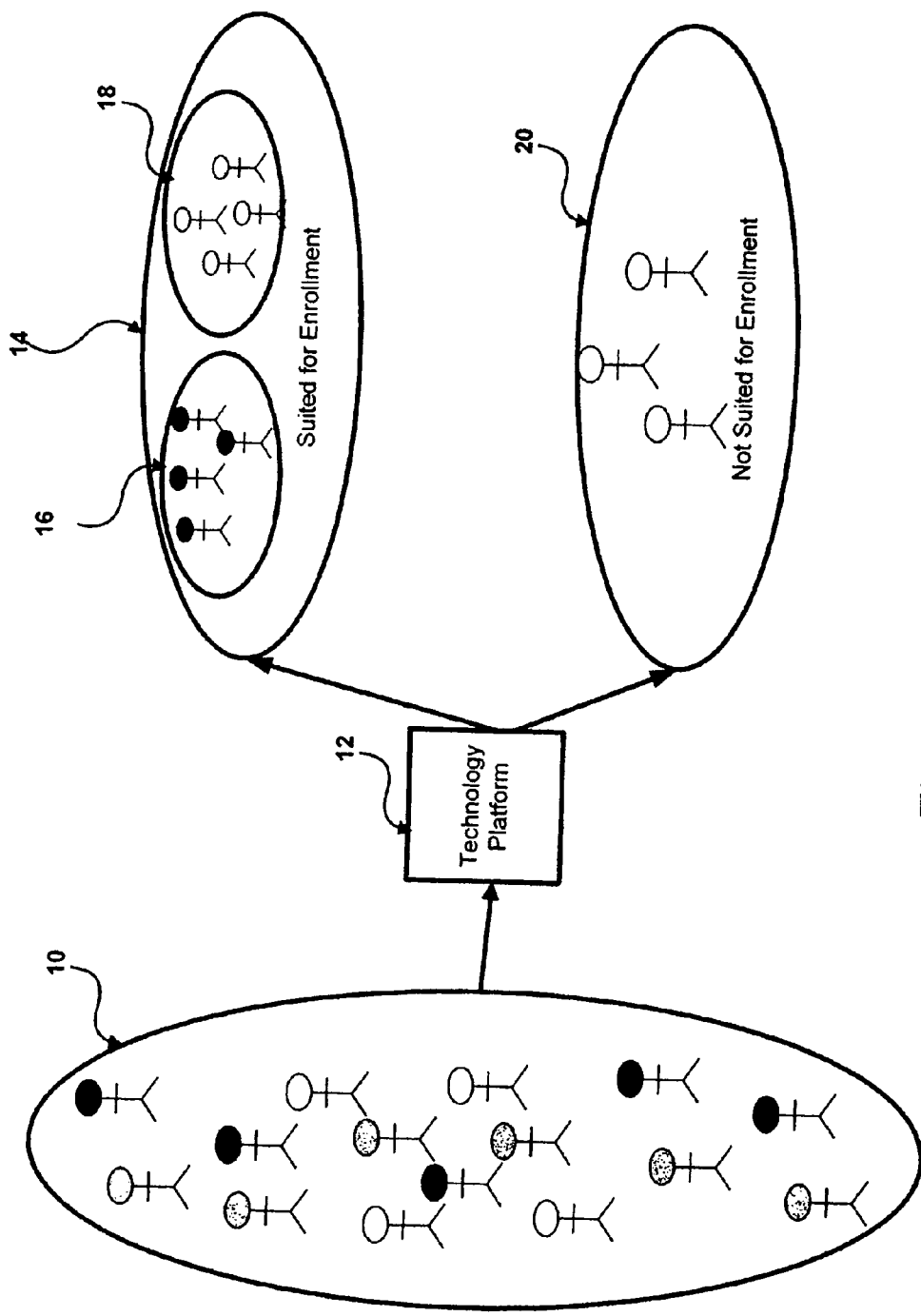
FIG. 1 is a diagram of a technology platform for segmenting individuals based on personality.

Referring to FIG. 1, a technology platform 12 is configured (e.g., includes software) to segment individuals 10 into multiple groups based on personality traits of the individuals and determine whether a particular individual would be well suited for enrollment in a consumer directed health plan (CDHP) or a high deductible health plan (HDHP). For example, the technology platform 12 can group individuals 10 into a first group 14 that includes individuals who would likely be well suited for enrollment in a CDHP or HDHP and another group 20 that includes individuals who would not be well suited for enrollment in such a health plan. Such segmentation can be used to encourage or discourage enrollment of a particular individual in a consumer directed health plan or high deductible health plan. In addition, the segmentation can be used to target materials about healthcare options to the groups of individuals based on the personality (e.g., the traits and temperament of the individual). For example, the group 14 of individuals who would likely be well suited for enrollment in a CDHP or HDHP can be further segmented into multiple groups 16 and 18 based on personality traits that influence the type of materials and information that would increase the likelihood of the individual enrolling in the CDHP or HDHP. For example, some groups of individuals might prefer to receive a mailing with a large amount of data that they could independently review while others might prefer to speak with a live agent about the CDHP or HDHP programs.

Figure 2:
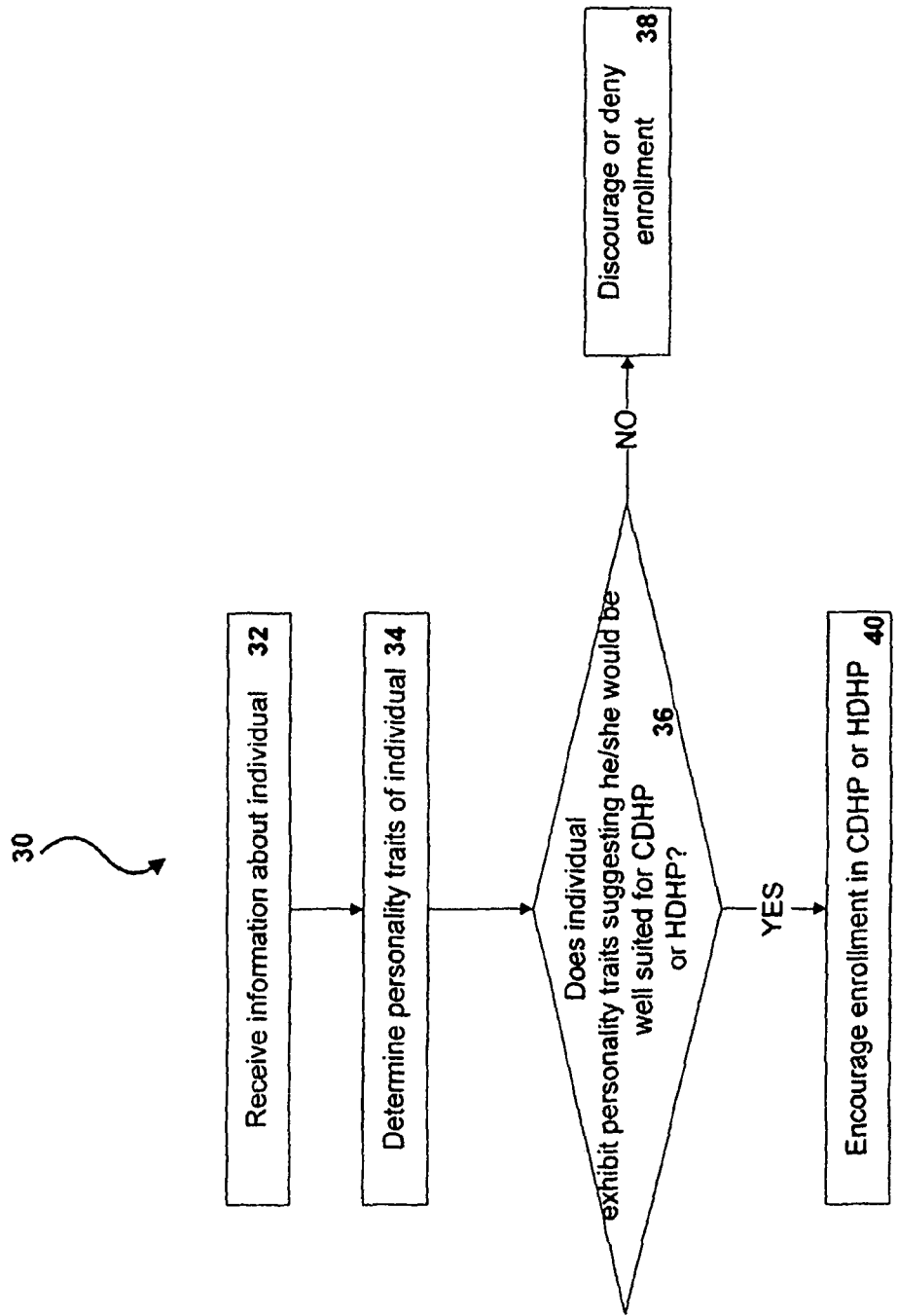
FIG. 2 is a flow chart of a segmentation process.

Referring to FIG. 2, a process 30 for segmenting individuals based on their suitability for enrollment in a CDHP or HDHP is shown. The technology platform 12 receives information about an individual (32) and determines personality traits of the individual based on the received information (34). Based on the personality traits, the technology platform 12 determines whether the individual exhibits personality traits that would suggest that the individual would be well suited for a consumer directed health plan or a high deductible health plan (36). If a particular individual exhibits personality traits that would suggest that the individual would be well suited for a consumer directed health plan or a high deductible health plan various methods (e.g., as described herein) can be used to encourage enrollment in the plan (40). For example, educational information or other information aimed at encouraging enrollment in the CDHP or HDHP can be presented to the individual based on the predicted personality trait of the individual. On the other hand, if a particular individual exhibits personality traits that would suggest that the individual would not be well suited for a consumer directed health plan or high deductible health plan, a company or insurer can take action to reduce the likelihood that the individual will enroll in the CDHP or HDHP or can simply deny enrollment in the CDHP or HDHP to the individual (38).

For individuals who exhibit personality traits that tend to suggest that they would be well suited for a consumer directed health plan or high deductible health plan, it is believed that selectively presenting information about consumer directed health plans and/or high deductible health plans to the individuals based on the prediction of the traits and temperament of the individual can increase the percentage of individuals that enroll in such a health plan. The traits and temperament of the individual can affect the type and amount of information needed to encourage or convince the individual to enroll in the health plan. For example, some individuals can have traits and temperaments that are more advice seeking in comparison to other individuals with different traits and temperaments. By predicting the personality traits of the individual before providing the individual with information about a consumer directed health care plan or high deductible health plan, the information provided to the individual about the consumer directed health care plan or high deductible health plan can be designed to address the concerns most likely to influence the individual's decision of whether or not to enroll in the health plan.

In addition to personality trait information, information associated with the individual such as demographic information can be used to determine what information to present to the individual about a consumer directed health plan and/or high deductible health plan. In some embodiments, a representative discussing the CDHP or HDHP with the individual may use a script that is customized to the traits and temperaments of the individual when discussing the consumer directed health plan with the individual.

While an insurance company may want to increase enrollment in consumer directed health plans and/or high deductible health plans for some groups of individuals, not all individuals are well suited for such plans. Consumer directed health plans and high deductible health plans transfer much of the risk from the insurer to the individual and often have high deductibles (e.g., in excess of $5,000-$10,000) associated with them. One danger of enrolling an individual in a CDHP or HDHP is that the insured individual will not adequately plan for the possibility that something might happen that would require him/her to pay such a high deductible. If an individual does not appropriately plan for and set aside a reserve for the possibility that he/she might have to pay the high deductible on a CDHP or HDHP, then having to meet the deductible could result in the individual either not seeking medical care or treatment when he/she should or facing possible bankruptcy or increased debt due to the medical expenses.

While income is related to the danger of inadequate funds, it is believed an individual's income alone is not an appropriate indicator of individuals who should avoid the risk of a high-deductible insurance plan such as a CDHP or HDHP. Rather, it is believed that other factors (e.g., attitudinal or personality based factors) can be used to determine such individuals. For example, some individuals may exhibit a personality type that causes the person to spend in a manner that could result in the individual's inability to pay a high deductible regardless of the individual's income.

The personality type of an individual can be determined using appropriately selected and phrased questions for which answers can be used to segment individuals according to whether they exhibit a particular personality trait (e.g., as described herein). Questions that could be used to determine if an individual exhibits an attitude that might indicate that he/she is likely to spend his/her income in a manner that he/she couldn't meet a deductible of a CDHP or HDHP could include questions about the spending habits of the individual, the credit card balances of the individual, the individual's attitude toward material possessions, the individual's spending habits, the individual's attitude toward savings, and the like. Exemplary questions could include:

"When I see something I want, I buy it regardless of my bank account,"

"I don't worry about my credit card balance,"

"I do not worry about my credit score,"

"I attempt to be the first person to have any new gadget on the market,"

In addition to personality traits associated with spending, other attitudinal traits such as the individual's attitude toward medical treatment can suggest that an individual would or would not be not well suited for a consumer directed health plan or high deductible health plan. For some personality types, attitudes about medical treatment in combination with a health plan such as a CDHP or HDHP where the individual bears a greater amount of the cost of medical treatment can result in avoidance of doctor visits, decreased likelihood an individual will elect to have diagnostic tests performed, and/or lowered likelihood the individual will take medications as prescribed.

In addition to personality traits associated with spending and medical treatment, other personality traits may contribute to indicating that a person is or is not not well suited for a CDHP or HDHP. For example, attitudes about employers, attitudes about how busy a person is, attitudes about organization, attitudes about convenience, attitudes about doctors, and the like may all contribute to segmenting individuals that are not well suited for CDHPs and/or HDHPs from those that are.

In order to determine what individuals are not well suited for CDHPs and/or HDHPs a survey can be administered to determine the personality of the individual. The survey can be either computer implemented (e.g., administered by an IVR or by a web-based application or by another computer-based system) or paper based and can focus on both attitudinal factors such as needs, attitudes, and behaviors as described above as well as factual profile information. The factual profile information can include factors such as income, credit score, credit balance, gender, marital status, number of dependents, arrest record, driving record, and the like. By analyzing an individual's response to the attitudinal questions and factual profile information, an algorithm can be used to determine whether the individual would be likely to misuse a consumer directed health plan or high deductible health plan. For example, a computer can solicit responses from an individual, compile the responses, and automatically determine the individual's suitability for a particular health plan based on an algorithm stored on the computer.

For individuals who exhibit personality traits that tend to suggest that they would be not well suited for a consumer directed health plan or high deductible health plan, insurance plan providers and/or employers can take actions based on the information such as denying enrollment in a consumer directed health plan or high deductible health plan to the individual or providing educational information to the individual about the appropriate use of such a plan. If the personality type of the individual is determined subsequent to the individual's enrollment in a CDHP or HDHP, the employer or insurer could use the information on the individual's personality type to determine whether or not to speak with the individual about changing the type of insurance or to provide counseling to the individual about appropriate use of the health plan. For example, the personality survey could be administered to employees as part of an employee survey and the results could be used to target counseling to individuals enrolled in CDHPs and/or HDHPs who abuse such a plan.

The personality type of the individual can be determined in a variety of ways. An exemplary process includes gathering a large amount of data from a cross-section of individuals. This information can include demographic data, credit data, answers to survey questions, and the like. Based on the data, categories or indicators can be defined to indicate which individuals are likely to abuse a CDHP and/or an HDHP. In addition, categories or indicators can be defined to indicate which individuals from the group of individuals not likely to abuse the CDHP and/or HDHP, would respond favorably to different types of information about a consumer directed health plan (e.g., what types of information and tactics are more likely encourage the individual to enroll in the consumer directed health plan or high deductible health plan). For example, individuals who are easily confused and seeking advice may require a more personal attention and time to ask questions in comparison to individuals who are confident decision makers. By determining characteristics such as age, income, and interests that indicate a propensity to certain types of responses to information about consumer directed health plans the type of information presented to the individuals can be tailored to the individual's personality. In order to predict the personality traits of a particular individual, demographic data is also received about the individual. This information is used to divide or place the individuals into a predicted category based on the expected response of the individual to certain types of information based on their personality type.

Various types of questions can be included in a questionnaire for gathering data used by a process to determine the personality traits of an individual. By comparing the questionnaire answers for a particular individual to information about the identified group of individuals the system can determine the most likely personality type of the individual. Exemplary questions can focus on things such as the way in which an individual makes decisions, how outgoing the person is, how much information the individual currently knows about health care options, how the individual manages their money, how an individual views health care, and what they currently do to manage their well-being.

Exemplary questions are presented below:
I am responsible for my own health and well-being
Food is a driving force in my health and wellness
Eating healthy is a vital part of my life
It is important that others regard me as a healthy person
It is important to me that other people know I exercise
It is important to me that other people know I eat healthily
Compared to others I know, I am very healthy
Genetics are the biggest factor in a person's health
There is little I can do to positively affect my health condition vs. There is much I can do to positively affect my health condition
My food choices are driven by . . . taste vs. health vs. convenience
I actively manage my weight
I always have my annual physical on-time
I am a sophisticated consumer of health products and services
My lifestyle choices are driven by . . . emotion vs. rationality vs. effort vs. time
I enjoy dealing with financial matters
I do not worry about planning for tomorrow
My household has a long-term financial plan
I am not very disciplined about sticking to a budget
I believe in spending first and saving what's left
I have a tendency to live beyond my means
When it comes to financial planning, I generally just "wing it"
I enjoy managing my household's healthcare matters
As the healthcare consumer, I am responsible for the cost of care
I expect that my out-of-pocket healthcare expenses will increase dramatically over the next three years
I find that making healthcare decisions is very complicated and difficult I try to predict what my healthcare expenses will be before the statement arrives
I let my HR or employer tell me what's best and just follow
The cost of healthcare is a major concern for me
I am anxious I won't be able to afford the quality of healthcare services I need
I want to control of my healthcare spending
I have developed a budget to manage current, ongoing, and future healthcare costs
I wish I had more control over my healthcare costs/spending
I strongly believe that the cost of preventative health measures should be covered by insurance
I'm happy with my current level of healthcare spending
I don't worry about healthcare costs until I have a problem
I worry about my health care expenses more than other people I know
If I understood my health plan's pricing better, I'd use my benefits more carefully for a share of savings
I have sought medical treatment not covered by insurance in the past
I am not interested in a HDHP because I want to go to the doctor without hesitation
A HDHP lets me control how my health care dollars are spent
I understand that an HDHP helps me control my healthcare costs in the long run
I regularly budget for out-of-pocket healthcare expenses
I would be more likely to take preventive care measures with a H.S.A.
I never doubt myself when making important health decisions
I always try to address health issues on my own before seeing a health professional
I immediately see a doctor whenever I have a health concern
I always get a second opinion on health topics
I do not like hospitals
When you seek medical care, the medical professional decides on your care and treatment, and you simply follow his or her advice
I would turn to my doctor for assistance in selecting a medical plan
I would rely on an agent's or broker's expertise to take care of my health insurance needs
It is more convenient buying health insurance directly from a company than through an agent or broker
I would feel comfortable buying insurance without personally knowing an agent or broker
All I need is a reputable health insurance company, not an agent or broker
The quality of agents is the real difference between reputable health insurance companies
It is likely that I will obtain professional advice for investment planning in the next 12 months
When it comes to making investment decisions, I rely only on my own knowledge rather than a financial advisor's recommendations
Managing my investments is too complicated for me to handle without a professional advisor
My health insurance company empowers me to take better care of my health
I have a personal relationship with representatives from my health insurance provider
My health insurance provider understands me and my household's healthcare needs
My health insurance provider does everything it can to help meet my household's health needs
My employer has placed the burden of annual premium increases on me
Selecting a health plan is too difficult without the help of an expert
Selecting an HDHP on my own is too complicated
I wouldn't know what to look for in a HDHP provider without the help of an advisor
I found health diagnostic surveys that match my projected health needs to a health plan to be very useful
I prefer to meet with an advisor in person to discuss H.S.A. options.
I strongly believe in having a personal relationship with someone from the firm that administers my H.S.A.
It is important that someone from an H.S.A. administrator sit down with me to explain the features, benefits, and restrictions
It is important that a company sit down with me to determine whether or not an H.S.A. is right for me
Employees at my health insurance provider do not seem very knowledgeable about my coverage details
Employees at my bank do not appear to be knowledgeable about H.S.A. details
I feel that I'm worse off financially than my friends and acquaintances
I spend a significant amount of time worrying about my finances
I never seem to have enough time to manage my financial affairs
I often worry that I won't be able to maintain my current standard of living
I do not feel confident that I will be able to reach my long term financial goals
I am very proud of my financial situation
I live paycheck to paycheck
There is little that I can do to positively impact my financial situation vs. There is much that I can do to positively impact my financial situation
I feel secure in my current job
I am a sophisticated consumer of financial products and services
I am a self-starter when it comes to learning about finances
My household has a long-term financial plan
I feel confident that I can save enough money to meet my retirement needs
My present financial needs outweigh my future financial needs
I'm worried I may go into bankruptcy because of my high healthcare expenses
I'm worried that I may lose my health insurance or may not be able to afford it because of my chronic illnesses/illnesses in my family
I'm afraid that if I have a major medical expense, I won't have the means to pay for it
Today's healthcare costs are unsustainable
Today's healthcare system is confusing and unfriendly to consumers
I wouldn't have any trouble getting approved for health insurance
A HDHP meets my short- and long-term healthcare needs
HDHP is the only health insurance option that I can afford
I worry that I will not be able to cover major medical expenses with a HDHP
HDHPs are well-designed to cover the bulk of the costs of major medical procedures With the higher deductible associated with HDHPs, I feel like I'd spend more money on healthcare I'm unprepared to manage another financial account required with HSAs I would prefer to pay a monthly charge and a low co-pay than having to figure out my charges every month for healthcare I currently consume health insurance as if it were free I do not think about the cost of visiting the doctor since my co-pay is so low I/my family don't have a lot of healthcare needs right now, so HDHPs make sense for me/my family My employer helped me understand why HDHPs make sense so I chose it HSAs are not worth the hassle of handling another financial account An HSA offers an attractive tax shelter.

I wish the H.S.A. annual contribution limit were higher

I am nervous about penalties related to using the funds in my H.S.A.

It's really confusing what is and isn't allowed to be used with my H.S.A.

I believe HSA's and FSAs allow the same types of pre-tax healthcare expenditures I (would) have multiple H.S.A. accounts (one for investments vs. one for savings)

I like H.S.A. accounts because I feel like I'm responsible for my own decisions

Please rate the following H.S.A. features: Pre-tax healthcare spending

Please rate the following H.S.A. features: Tax advantages/shelter

Please rate the following H.S.A. features: Automatic healthcare tracking

Please rate the following H.S.A. features: Earns interest

Please rate the following H.S.A. features: Grows at investment gain rates

Please rate the following H.S.A. features: Attached line of credit

Please rate the following H.S.A. features: Money not forfeited at the end of the year (roll over)

Please rate the following H.S.A. features: Annual contribution limit

Please rate the following H.S.A. features: Contributions may be made until April 15 of the following tax year Please rate the following H.S.A. features: Allowable catch-up contributions Please rate the following H.S.A. features: Self-regulated expense management (with kept records and receipts)

Please rate the following H.S.A. features: I decide how much to contribute

Please rate the following H.S.A. features: Whether to pay for health care expenses from the account or save the account for future use Please rate the following H.S.A. features: Ownership—not employer dependent Please rate the following H.S.A. features: No manual claims forms needed Please rate the following H.S.A. features: Integration with HDHP Please rate the following H.S.A. features: Debit card Please rate the following H.S.A. features: Rewards-based debit card I love doing research on my own about the quality and costs of doctors and prescriptions I find managing my personal finances to be intimidating I know exactly what my health insurance covers and doesn't cover I consider myself to be very knowledgeable when it comes to healthcare financing/the healthcare insurance industry I don't understand how the health insurance industry works I don't know which type of health insurance is right for my household I know what the cost of a doctor's visit would be to me if I did not have health insurance Consumers in America should have the right to information on healthcare costs the same way they do in every other industry I wouldn't know where to start when it comes to selecting HDHPs HDHPs are the best new product available related to healthcare management The benefit of acquiring an HDHP outweighs the complexity of opening one I am not inclined to get an HDHP because I don't understand it I understand the difference between a HDHP and other health insurance options HDHPs are worth it for the lower premiums I'm nervous that with a HDHP, I'd be worse off HDHPs won't work because doctors do not honor insurance companies' negotiated rates HSA's are the best new product available related to healthcare management The benefit of acquiring an H.S.A. outweighs the complexity of opening one I don't understand enough about HSA's to open one I am unlikely to acquire an H.S.A. in addition to the other complex healthcare products that I already manage I take every precaution I possibly can to mitigate the risk of getting sick The best way to avoid costly medical procedures is to eat healthy and stay active I firmly believe that preventive health is the best health plan I'm not willing to risk my financial future in something as volatile as the stock market It's worth my time to move funds around to maximize my return I mostly have my health insurance plan solely for the case of an emergency I would rather have a lower premium health plan and deal with emergency costs as they arise It's frustrating to me that my health plan will not cover less expensive preventive measures, but will cover costly reactive medical procedures I believe that the health insurance products are perfectly designed the way they are Health insurance should be focused on preventing medical conditions, rather than just treating them My health plan provider listens to me when I suggest improvements to the insurance product or service HDHPs help consumers control the risk of longer-term increased healthcare costs HDHPs help consumers understand the real healthcare issues that drive costs up The H.S.A. is a good utility for managing the risk of unexpected healthcare costs With an H.S.A., I feel confident that I can manage unexpected healthcare costs I trust my doctor to provide me with assistance when I have a costly medical need I am unlikely to switch doctors' offices once I start visiting one I count on my PCP to provide trustworthy referral recommendations for specialists I only seek referral recommendations from friends and family I really don't know who to trust when it comes to medical advice When possible, I always seek a second opinion before undergoing major medical surgery I am very loyal to my primary bank I have a preferred company that I turn to first for any financial need I really don't know who to trust when it comes to financial planning I trust my healthcare insurance provider will take care of me when I am in need I trust that my HDHP provider would let me see a doctor/medical provider that I know My HDHP provider would help me find a trustworthy doctor/medical provider I trust that my HDHP provider will help me with costly medical expenses I view my HDHP provider to be my health plan partner If I wanted to, I could switch from a HDHP to another health plan option with my current provider I trust that the insurance companies designed HDHPs to protect the interest of the consumer I would first turn to my current health insurance provider to explore HDHP options I wouldn't know where to look first for a HDHP My current insurance provider has encouraged me to explore HDHPs I am unlikely to switch HDHP providers once I open an account My employer has promoted HDHPs to all of its employees My employer continues to shift the burden of healthcare expenses to me I am nervous that my employer will no longer offer healthcare coverage Which one of the following statements would you say is closest to the way you feel about your current health benefits: You would rather have more health benefits through your employer and lower pay.

Which one of the following statements would you say is closest to the way you feel about your current health benefits: You are satisfied with the amount of health benefits you receive through your employer.

Which one of the following statements would you say is closest to the way you feel about your current health benefits: You would rather have fewer health benefits through your employer and higher pay.

I would most likely open an H.S.A. from my primary bank out of convenience

Banks offer the best deals on HSA's

It makes the most sense to open an H.S.A from an insurance provider

I trust my bank to offer the most security on an H.S.A. account

I am unlikely to switch H.S.A. providers once I open an account

My employer offers HSAs

My employer has promoted health savings accounts to all its employees

I would get an H.S.A. regardless of whether or not my employer offered it

My employer is willing to make contributions to my H.S.A.

My primary health plan is always on my side for any problems or concerns I have

My primary bank is always on my side for any problems or concerns I have

I would turn to a brokerage firm for HSA's for the investment possibilities

I would turn to a bank for an H.S.A. for the transaction management capabilities I have one credit card that I use to track healthcare expenses I regularly discuss healthcare costs with all my providers before conducting any procedures I've asked a healthcare professional in the past about extended payment plans I shop around for healthcare providers to compare price and quality Medical costs vary greatly from provider to provider Insurance companies always receive better rates than individual consumers.

I will only see physicians that are in my health plan's network

My health plan has a wide network of physicians

It's hard for me to find a good doctor that accepts my health insurance plan

I always fill the generic prescription whenever I can

I always compare prescription prices across several pharmacies

My health insurance does not cover the prescription brands that I prefer

My prescription plan is expensive

I don't understand the prescription plan pricing that my health insurance company offers I feel like my health insurance provider always has my best interests in mind My health insurance provider clearly explains to me the range of costs that treatments I need I receive most of the information from my health plan through my employer I shop around for the best price on Rx drugs I shop around for the best quality/price for doctors I shop around for the best quality/price for hospitals I will compare HDHP plans across several providers I know how much I need in my HSA to cover my insurance premiums I will contribute the maximum limit ($4,500 for family, $2,250 for individual or more if over 55) to receive the maximum tax benefits I actively do research for doctor/hospital cost comparisons I actively do research for prescription drug cost comparisons I tend to conduct research on the web regarding doctors and hospitals I maintain tight control over my health care spending using online financial tools (e.g., Quicken Medical Expense Manager) vs. general tools (Excel, Quicken)

I often search my insurance company's website for information

I use a cost estimator for health care costs (physician visits, procedures, etc.)

Health expense trackers

Paper-based expense tracking system

I actively manage my HDHP to ensure that the charges applied to my deductible are accurate I actively manage my H.S.A. to ensure that the charges applied to my deductible are accurate In some embodiments, a set of questions used to determine the personality traits of the individual with respect to whether the individual would be well suited for enrollment in a consumer directed health plan (CDHP) or a high deductible health plan (HDHP) can include a limited number of questions, e.g., from about 10 to about 30 questions (e.g., about 10 questions, about 15 questions, about 20 questions, about 25 questions). Using a smaller number of questions can provide the advantage of increasing the likelihood an individual will complete the survey and answer all of the questions.

Figure 3:
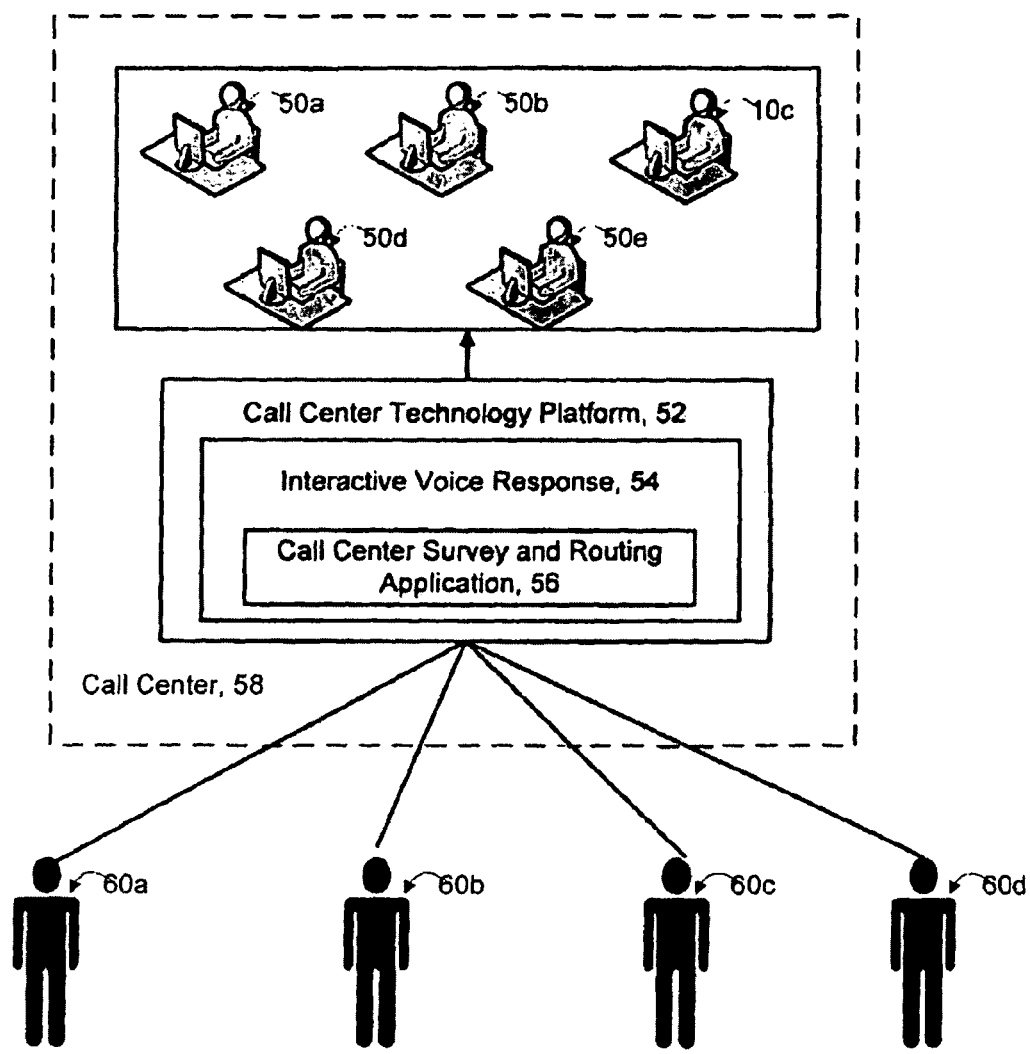
FIG. 3 is a block diagram of a routing process.

Referring to FIG. 3, in some embodiments a call center 58 can be used to facilitate segmenting groups of individuals and determine whether the individual would be well suited for enrollment in a consumer directed health plan (CDHP) or a high deductible health plan (HDHP). The call center 58 can also provide individuals trained to encourage or discourage enrollment of a particular individual in a consumer directed health plan or high deductible health plan based on the personality of the individual. In addition, the call center 58 can provide materials about healthcare options to the groups of individuals based on the personality (e.g., the traits and temperament of the individual).

Typically, a call center 58 receives telephone calls from callers 60a-60d and routes the calls to customer service representatives 50a-50e that service the calls. Typically, the call center 58 has the ability to concurrently handle a considerable volume of calls, to screen calls, to forward calls to available representatives, and to log calls. The call center 58 includes call center technology platform 52 that has the ability to route the calls to specific ones of the customer service representatives 50a-50e using a software-based determination by an automated call center survey and routing application 56.

In some embodiments, when a caller 60a-60d calls the call center 58, the caller 60a-60d can be directed to an interactive voice recognition system (IVR) 54 and the call center survey and routing application 56 uses the IVR 54 to prompt a caller 60a-60d to provide answers to a survey and to receive the responses from the caller 60a-60d. The survey responses can be used to determine the personality type of the caller 60a-60d. The personality type of the caller 60a-60d can be used to determine if the user is a likely to enroll in a CDHP or HDHP and/or what type of information could be provided to the caller 60a-60d to encourage or discourage enrollment in such a plan. The personality type of the caller 60a-60d can be determined using appropriately selected and phrased questions for which answers can be used to segment callers 60a-60d according to whether they exhibit a particular personality trait. For example, questions could include questions about the habits of the caller, the activities of the caller, the credit card balances of the individual, the individual's attitude toward material possessions, the individual's spending habits, the individual's attitude toward savings, and the like. Based on the responses provided by the caller 60a-60d during the automated survey, the call center survey and routing application 56 determines a personality type of the caller 60a-60d. The call center technology platform 52 uses the information about the personality of the caller 60a-60d and the likelihood of the caller being a candidate for enrollment in a CDHP or HDHP to direct the caller to an appropriate call center representative 50a-50e. In some embodiments, if the survey results indicate that the caller 60a-60d would not be a good candidate for enrollment in a CDHP or HDHP, then the call center technology platform 52 can determine not to expend further resources by routing the caller 60a-60d to a live representative.

In addition, in some embodiments, if the caller 60a-60d is routed to a call center representative 50a-50e, the call center technology platform 52 can provide information about the caller 60a-60d to the call center representative 50a-50e and the call center representative 50a-50e can structure the discussion with the caller 60a-60d based on the information provided about the caller 60a-60d. For example, the information provided to the caller 60a-60d about the CDHP or HDHP can be presented in a manner that the caller 60a-60d is likely to understand and that is believed to potentially increase the likelihood of the caller 60a-60d enrolling in the CDHP or HDHP.

In addition, in some embodiments, the call center 58 can maintain data about the callers 60a-60d who spoke with a call center representative 50a-50e about enrollment in the CDHP or HDHP. This information can be used to gather statistics about what employees enrolled in the CDHP or HDHP based on the information provided by the contact with the a call center representative 50a-50e. In addition, this information can be used to follow-up with the caller 50a-50e at a later date. For example, the caller 50a-50e can be contacted by a customer service representative at a later date. The customer service representative can answer any additional questions that the caller 60a-60d may have. Alternatively or additionally, the information about enrollment and contact with the customer service representatives can be used to target mailings or other information dissemination to individuals who are likely to be evaluating enrollment in the CDHP or HDHP. It is believed that such a targeted use of a letter or phone call at a predetermined date after the caller spoke with the customer service representative may increase the possibility of enrollment of the caller in the CDHP or HDHP.

It is believed that providing a multi-step process that includes using the IVR 54 to receive responses to survey questions used to segment individuals with respect to their personality and likelihood of enrolling in a CDHP or HDHP and subsequently routing at least some of the callers to live customer service representatives 50a-50e in a call center 58 can provide various advantages. For example, the information provided to the caller 60a-60d can be tailored to the personality type of the caller 60a-60d based on their responses to the automated survey. Tailoring the information provided to the caller 60a-60d can increase the likelihood of the caller 60a-60d enrolling in the CDHP or HDHP because the caller 60a-60d can receive the type and amount of information desired to make such a decision.

In some embodiments, the call center 58 or third party operating in conjunction with the call center can offer a program to companies that have CDHPs and HDHPs available for employees to potentially increase enrollment in such plans. Payment to the call center 58 or third party can be based on an agreed upon metric. For example, rather than paying a fixed sum to the call center 58 or third party to provide the service, the price could be based on the number of callers who use the system, the number of leads generated by the system, and/or the number of callers who subsequently enroll in the CDHP or HDHP after calling. In addition, the fee could be based on multiple factors. For example, the company could pay a small fee (e.g., $1-$25) for each caller that uses the system and a larger fee (e.g., $50-500) for each caller who subsequently enrolls in the companies CDHP or HDHP. In another example, the company could pay a small fee (e.g., $1-$25) for each caller that uses the system, a moderate fee (e.g., $20-100) for each caller who is connected to a live agent based on the results from the survey, and a larger fee (e.g., $50-500) for each caller who subsequently enrolls in the companies CDHP or HDHP. It is believed that enabling the company and third party to customize a payment plan based on potential increased enrollment can provide the benefit of providing a method of using customer profiling to increase enrollment in the CHDPs and HDHPs that is less cost-prohibitive than paying a large up-front fee for the service.

Figure 4:
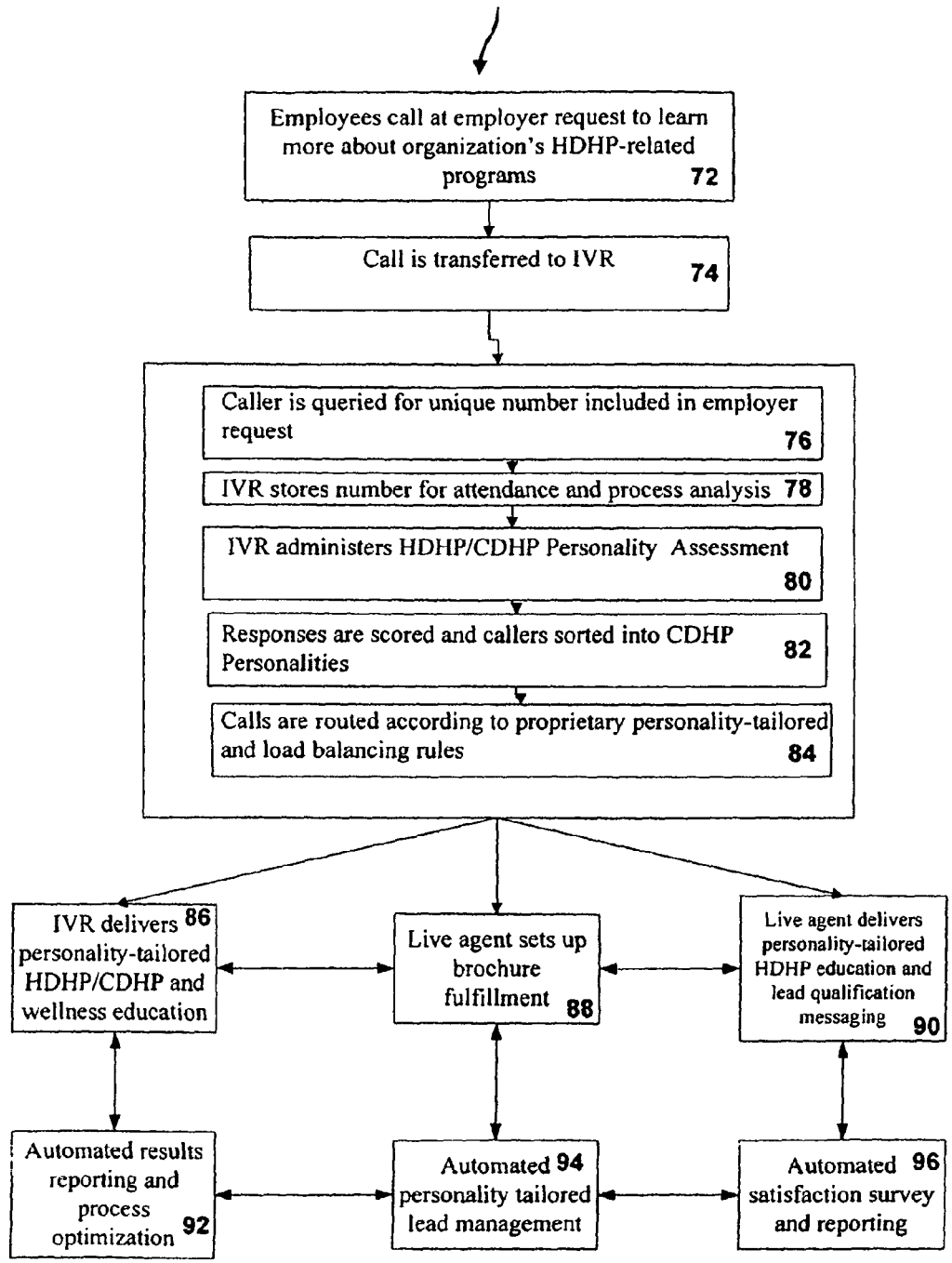
FIG. 4 is a flow chart of a segmentation and information distribution process

Referring to FIG. 4, a process 70 for using an IVR to assist in segmenting individuals based on their suitability for a CDHP or HDHP and directing information to the individual based on their personality is shown. A company can use such a process to encourage enrollment in the company's CDHP or HDHP health plans and/or other wellness programs. Employees can call either by their own initiative or at the employer's request to learn more about the company's HDHP or CDHP health programs (72). When the employee calls, the call is transferred to an IVR (74). The IVR is configured to determine the personality type of the caller to determine whether the caller would be well suited for enrollment in the CDHP or HDHP. The IVR can also track the calls and individuals who participate in the survey. For example, the IVR can query the caller for a unique identifier such as an employee number, social security number, or other identifier (76). The IVR stores the number for attendance and process analysis (78). For example, the statistics collected about the people who call the IVR to obtain information about the CDHP or HDHP can be used for billing purposes and/or to determine programs for approaching individuals and distributing information about the CDHP and HDHP programs. The IVR also administers an HDHP/CHDP personality assessment (80). The HDHP/CHDP personality assessment can be based on a short survey of between 5-20 questions (e.g., 10 questions, 15 questions, etc.). The caller can respond to the questions using the touch-tone buttons on the telephone. Based on the responses received from the caller, the IVR scores the responses and sorts the callers into multiple groups based on the predicted HDHP/CHDP personality of the caller (82) and routs the calls according to rules for routing calls that are tailored based on the personality and load balancing (84).

The IVR can route the calls to pre-recorded messages or to live agents that can deliver further information to the caller based on the predicted HDHP/CHDP personality of the caller. For example, for some callers the IVR can route the individuals to prerecorded messages where the IVR delivers personality-tailored HDHP/CDHP and wellness information (86). The messages delivered to the individual by the IVR can differ (e.g., in content and/or in length) based on the predicted HDHP/CHDP personality of the caller. For other callers, the IVR can route the caller to a live agent that sets up for a brochure to be delivered (e.g., via email or mail) to the caller (88). For yet other callers, the IVR can route the caller to a live agent that delivers personality-tailored HDHP/CDHP and wellness education and lead qualification messaging to the caller (90). The IVR and/or the live agent can route the caller to other ones of the functionalities. For example, the live agent can route the caller to the IVR to receive further information via the pre-recorded messages and or to another agent for brochure requests. In another example, the IVR can include options that the caller can select enabling the caller to be connected to a live agent for information or to a live agent for a brochure request. In another example, a live agent who fulfills a brochure request can ask the caller if they would like to hear more information and transfer the caller to the IVR or another live agent based on the caller's request.

After receiving information either from a live agent or from the IVR, the process 70 can include analyzing the results of the contact with the caller. For example, the process 70 can include automatically reporting results of the call and optimization for the call (92), automatically generating personality lead management information (94) and/or automatically administering satisfaction surveys and reporting (96).

Figure 5:
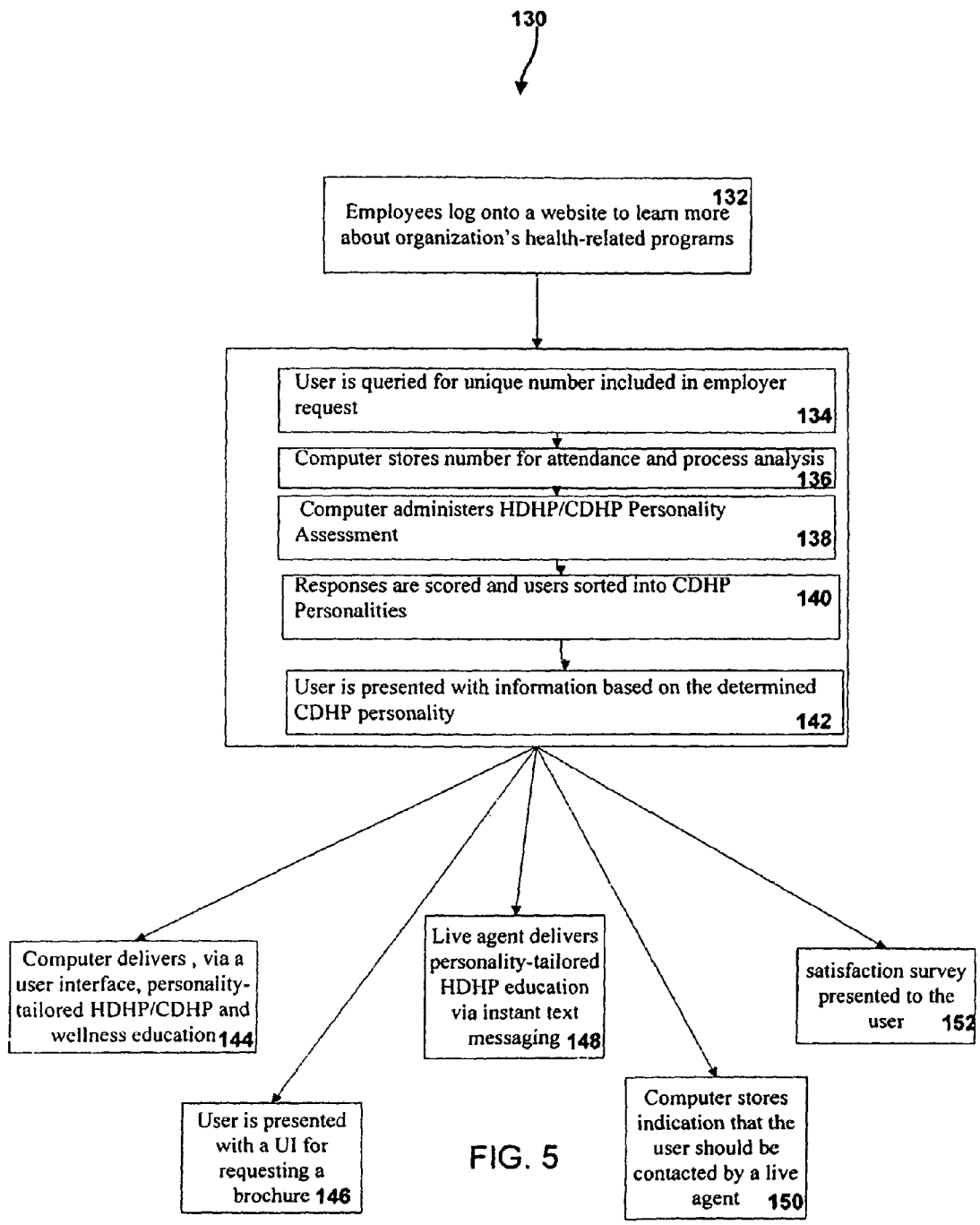
FIG. 5 is a flow chart of a segmentation and information distribution process

While in some of the embodiments described above, an IVR was used to assist in segmenting individuals based on their suitability for a CDHP or HDHP and directing information to the individual based on their personality, however other methods of segmenting individuals and presenting information can be used. For example, FIG. 5 shows a computer implemented process 130 for using a computer system to assist in segmenting individuals based on their suitability for a CDHP or HDHP and directing information to the individual (via the user interface, subsequent telephone call, instant messaging, and/or mailing) based on their personality. A company can use such a process to encourage enrollment in the company's CDHP or HDHP health plans and/or other wellness programs. Employees can log onto a website that administers a survey (e.g., as described herein) and determines the employee's personality and suitability for programs (132). When the employee log onto the website, a computer determines the personality type of the individual and whether the individual would be well suited for enrollment in the CDHP or HDHP. The computer can also track individuals who participate in the survey via the web-based interface. For example, the computer can query the caller for a unique identifier such as an employee number, social security number, or other identifier (134). The user inputs the information using a keyboard or other input device and the computer stores the number for attendance and process analysis (136). For example, the statistics collected about the people who log onto the website to obtain information about the CDHP or HDHP can be used for billing purposes and/or to determine programs for approaching individuals and distributing information about the CDHP and HDHP programs. The computer also administers, via a user interface, an HDHP/CHDP personality assessment (138). The HDHP/CHDP personality assessment can be based on a short survey of between 5-20 questions (e.g., 10 questions, 15 questions, etc.) that are presented to the user on a user interface. The individual can respond to the questions using a mouse or keyboard to input information. Based on the responses received from the individual, the computer scores the responses and sorts the employees who log onto the site into multiple groups based on the predicted HDHP/CHDP personality of the individual (140). Based on the determined HDHP/CHDP personality of the individual, the computer presents the individual with information that is tailored based on the individual's personality (142).

The computer can present different information to the user based on the predicted HDHP/CHDP personality of the user. For example, the computer can deliver, via a user interface, personality tailored CDHP and HDHP information (144). The personality tailoring can be both in terms of content and format of the information presented to the user. As such, the information presented to the user can differ (e.g., in content and/or in length) based on the predicted HDHP/CHDP personality of the caller. For example, some users may be presented with more detailed information such as statistics while others may be presented with more generalized information. In addition, the organization and layout of the information can differ. For example, the graphics included on the user interface can differ for different personality types. For some personality types the graphics might focus on charts and for other personality types pictures and graphics might be employed to increase the likelihood of the user reading the information. While for some users, the computer directs the user to a website with further information, for other users, the computer system can present the user with a user interface for requesting a brochure to be delivered (e.g., via email or mail) to the user (146). For yet other users, the computer can route the user to an interface where the user can chat via text messaging with a live agent that delivers personality-tailored HDHP/CDHP and wellness education and can answer any questions the user may have (148). After presenting information to the user, the process 130 can include analyzing the results of the contact with the user. For example, the process 130 can include automatically reporting results of the user's interaction with the website such as the amount of time spent on each webpage, the links clicked on by the user, etc. The computer can also store an indication of whether the user should be contacted by a live agent (e.g., via telephone) at a later time (150). In some embodiments, the computer can also automatically administer a satisfaction survey to the user to collect information regarding the user's experience with the website (152).

Figure 6:
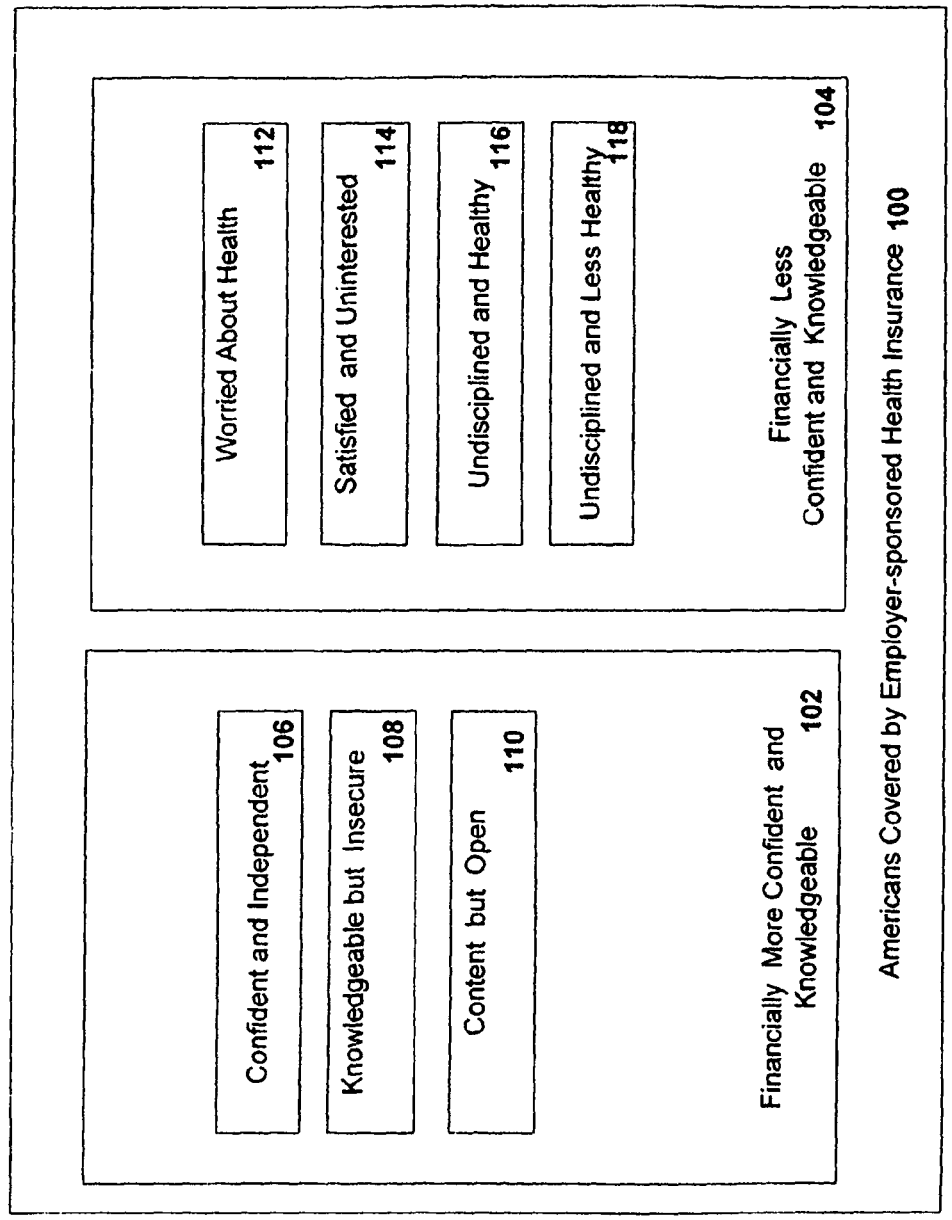
FIG. 6 is a block diagram of personality segments for CDHP or HDHP plans.

FIG. 6 shows exemplary HDHP/CHDP personality groupings. A set of individuals covered by employee-sponsored health insurance 100 can be divided into two classifications that will impact whether a HDHP or CDHP would be a suitable insurance option for the individual and the type of information that would help the individual to make a decision regarding whether or not to enroll in a HDHP or CDHP insurance plan. A first grouping 102 includes individuals who are generally financially more confident and knowledgeable and a second grouping of individuals 104 includes individuals who are financially less confident and knowledgeable.

The needs, attitudes, and behaviors can differ between the individuals in the grouping 102 of individuals are generally financially more confident and knowledgeable and the grouping 104 of individuals who are financially less confident and knowledgeable. For example, in general, it may be less important for individuals in group 102 to receive expert advice about a CDHP or HDHP in comparison to individuals in group 104. The manner in which individuals in group 102 prefer to receive information may also differ from the manner in which individuals in group 104 prefer to receive information. For example, individuals in group 102 may be more responsive to receiving information on the web and having minimal contact with a live agent. In comparison, individuals in group 104 may prefer a people-oriented approach in which they can discuss concerns and questions with a live agent. The decision making style may also differ between individuals in group 102 and group 104. For example, individuals in group 102 may base more of their opinions on individual and independent research in comparison to individuals in group 104 who may be more likely to seek the advice and recommendations of an expert. The risk tolerance may also differ between individuals in group 102 and group 104. For example, individuals in group 102 may be more aggressive than individuals in group 104. The CDH-related knowledge may also differ between individuals in group 102 and group 104. For example, individuals in group 102 may be more knowledgeable about health insurance than individuals in group 104. The confidence level may also differ between individuals in group 102 and group 104. For example, individuals in group 102 may be more confident than individuals in group 104. The degree of financial planning may also differ between individuals in group 102 and group 104. For example, individuals in group 102 may have a well laid out plan in comparison to individuals in group 104 who may be more likely to need better planning or have no financial plan at all. The frequency with which an individual considers changing health care providers or the type of health care coverage they use may also differ between individuals in group 102 and group 104. For example, individuals in group 102 may shop for new health care providers and plans more often than individuals in group 104. The level to which an individual is involved in managing their own health and following medical instruction may also differ between individuals in group 102 and group 104. For example, individuals in group 102 may follow medical instruction without question while individuals in group 104 may be more likely to disregard medical instruction.

Within each group 102 and 104 the degree to which an individual exhibits particular needs, attitudes, and behaviors can differ. In order to account for such differences, each group 102 and 104 can be further sub-divided into multiple subgroups based on personality traits of the individual. In an example, the group 102 of individuals who are generally financially more confident and knowledgeable can be subdivided into three groups including a group 106 that includes individuals who are more confident and independent, a group 108 that includes individuals who are knowledgeable but insecure, and a group 110 of individuals who are content but open. In an example, the group 104 can be divided into four groups including a group 112 of individuals who are worried about their health, a group 114 of individuals who are satisfies and uninterested with respect to their health insurance, a group 116 of individuals who are undisciplined and healthy, and a group 118 of individuals who are undisciplined and unhealthy. The needs, attitudes, and behaviors of each of the subgroups can differ. In addition, other groupings of individuals are possible. For example, individuals could be divided into more groupings, into fewer groupings, or into different groupings depending on a desired degree of individualization and targeting based on personality.

Figure 7:
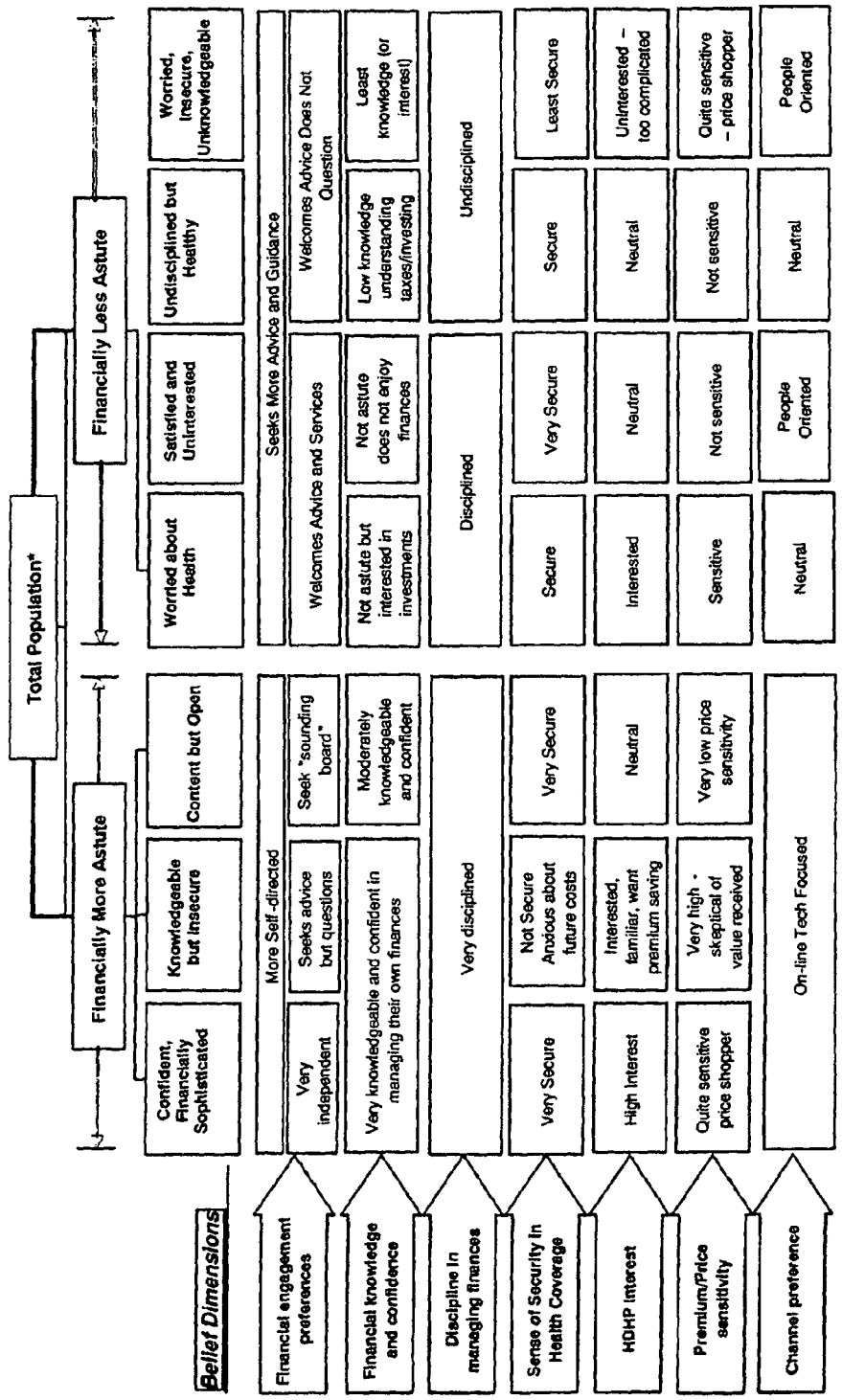
FIG. 7 is a diagram of exemplary characteristics of individuals in the various personality segments of FIG. 6.

FIG. 7 shows exemplary beliefs and preferences for each of groups 106, 108, 110, 112, 114, 116, and 118. Knowledge about the general beliefs of the individuals in each of groups 106, 108, 110, 112, 114, 116, and 118 can inform a decision regarding whether to contact an individual regarding a CDHP or HDHP and if so, what format and type of information should be presented to the individual.

While in some of the embodiments described above, personality segmentation was used to target enrollment and dissemination of information related to CDHP and HDHP plans, similar segmentation processes can be used to encourage enrollment in wellness plans and to disseminate information related to wellness plans. For example, wellness information about disease detection such as prostate or breast cancer detection can be presented to individuals based on their personality type. In addition, information about disease management such as management of asthma, diabetes, high blood pressure or other long-term health problems can be presented to individuals based on their personality type. In addition, in some embodiments, individuals can be segmented into groups according to their likelihood of participating in wellness or exercise programs and information can be presented to the individual about programs that might be of interest to a particular person based on their personality. It is believed that distributing information about wellness to individuals in a format that the individual is more likely to review and accept can increase the likelihood of the individual promoting their own health which in turn can reduce the cost of health services for the individual.

While in some of the embodiments described above, personality segmentation was used to target enrollment and dissemination of information related to CDHP and HDHP plans, similar segmentation processes and personality type groupings can be used to provide information and guidance to an individual subsequent to their enrollment in a CDHP and HDHP plan. For example, an employer or insurance company provides information about use of the consumer directed health plan or high deductible health plan to an individual that is tailored to the predicted personality type of the individual. This information can be related to various aspects of effective usage of a CDHP and HDHP plan. In addition to tailoring the information based on the predicted personality type, the information can also be tailored based on the individuals actual usage of the CDHP and HDHP plan (e.g., what medical services the user has/has not used, what preventative care the user has obtained, how often the individual seeks medical treatment, what facilities the individual has visited).

As described above, a consumer directed health plan engages consumers more directly in their health care purchases and often makes cost and quality information evident to the consumer (e.g., through the Internet). High deductible health plan health plans often offer lower premiums and higher deductibles than a traditional health plans. While CDHP and HDHP plans can be cost effective for both the consumer and the employer, many consumers are inexperienced with managing their own healthcare and may be unaware of options for reducing their costs associated with healthcare under such plans. In addition, many consumers are inexperienced with managing their finances to plan for medical related expenditures. In order to counsel and educate the individual on usage of the CDHP or HDHP plan, information is presented to the individual that differs (e.g., in content, presentation, and/or in length) based on the predicted HDHP/CHDP personality of the individual. The format of the information delivery (e.g., live agent call, in-person counseling, dissemination of written information by email or mail) can also vary based on the predicted HDHP/CHDP personality of the individual. Providing different information to different individuals enrolled in a CDHP or HDHP can increase the individual's receptiveness to the information because the information presented has content of interest to the individual and is presented in a format to which the individual is likely to respond positively. Some of the information that is distributed gives pointers about how to plan for medical expenses that are ultimately unavoidable. It can be important to distribute such information to individuals who have difficulty planning their finances because otherwise they may not prepare for such expenses at great risk to their financial wellbeing.

For example, consider an exemplary case of an individual enrolled in a CDHP with knee pain who seeks treatment. The individual is likely to schedule and appointment with either their primary care physician or a orthopedic doctor. At such an appointment, the doctor might recommend that the individual have an MRI scan and enter physical therapy for the injury. Since the doctor is associated with a particular hospital or medical group, the doctor is likely to recommend the most convenient MRI machine (e.g., the one located in the same hospital). Similarly, due to familiarity and convenience, the doctor might recommend a group in the same hospital to perform the physical therapy. Under a CDHP, the co-payment fees for the various medical treatments could be substantial and the individual may be unaware of ways to mitigate and reduce the costs. For example, by having the MRI done at another facility or selecting a different physical therapy group could reduce the costs while the treatment would be of a similar type and quality. In order to educate the individual on such options, the insurance company and/or individual's employer could offer information and counseling services to the individual in a format that the individual is likely to be receptive to based on their personality type. For example, if the individual has a personality type that is less financially foresighted, the information presented could include directions as to how and where to save money for medical expenses and could be presented in simple format and provided through a live telephone agent. In contrast, if the individual has a personality type that is financially astute, the information presented could include advanced financial strategies to save taxes while paying medical expenses and could be presented in a tabular format through electronic means such as the Internet. By tailoring the information based on the individual's personality type, the individual is more likely to be receptive to the information and their satisfaction with the CDHP plan may increase.

Figure 8:
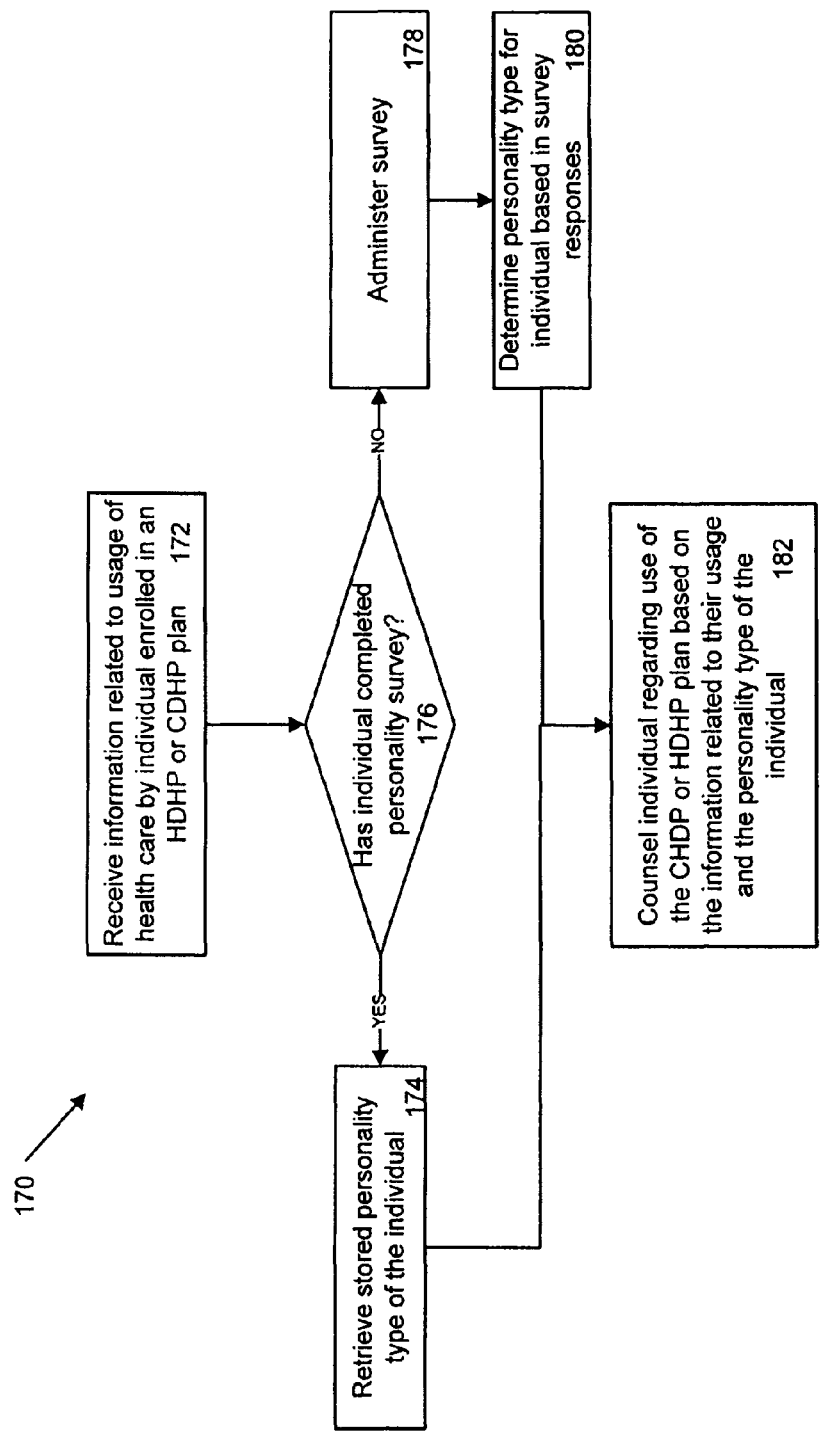
FIG. 8 is a flow chart of a counseling and/or information distribution process.

FIG. 8 shows a process 170 for counseling an individual regarding usage of a CDHP or HDHP plan based on a determined personality type of the individual. The process includes receiving 172 information related to an individual's usage of health care under the CDHP or HDHP plan. This information can include summary information related to the individual's health, usage codes related to medical expenditures, lists of tests or procedures performed, and/or other information generally available to an insurance company related to an individual's health care usage. Process 170 also includes determining 176 if the individual has completed a personality survey (e.g., as described above). If the user has completed the survey previously, information about the personality type of the individual is retrieved 172. If the user has not completed the survey, the survey is administered 178 and the personality type is determined 180 based on the responses to the survey. The information about the usage of the health care and about the personality type of the individual is used to counsel 182 the individual regarding their use of the CDHP or HDHP plan.

Tailoring information presented to an individual enrolled in a CDHP or HDHP plan based on the individual's personality type can provide various advantages. For example, if the information is presented in a format that is interesting and understandable to the individual, the individual is more likely to spend the time learning about how to effectively use their CDHP or HDHP plan. In addition, helping an individual to understand their choices regarding healthcare under a CDHP or HDHP plan can increase their approval or happiness with the plan and encourage the individual to remain on a CDHP or HDHP plan which is often less costly for the employer. Message tailoring can also be used to meet specific emotional needs of individuals. For example, there are many individuals who are anxious about their health and their ability, intellectually and financially to provide for themselves and their dependents. For such individuals, messages can be tailored to be soothing but constructive criticism so as to make their thoughts, feelings and action about healthcare more effective.

In addition, in some embodiments, the information presented to an individual can vary based on income in addition to the individual's personality group. For example, if two individuals classified in the same personality group have incomes of $20,000 and $200,000, the advice provided to the individuals regarding healthcare usage under the CDHP or HDHP may vary. For example, the information provided to a lower-income earning individual may be focused primarily on reducing the individual's out of pocket expenses for obtaining the same healthcare while the information provided to the higher-income earning individual may be focused on preventative healthcare options. However, in both cases the personality type can be used to tailor how the information is presented to the individual.

While various factors that can affect the counseling and information presented to the individual are presented above, other factors can be used to modify and tailor counseling information presented to the individual. For example, the counseling and information presented to the individual can be tailored to anxiety of the individual, perception of one's health status, feeling about keeping the same primary care physician, feelings about the motives of insurance companies, and the like.

Apparatus of the invention can be implemented in a computer program product tangibly embodied in a machine-readable storage device for execution by a programmable processor and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired, and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files, such devices include magnetic disks, such as internal hard disks and removable disks magneto-optical disks and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

In addition, aspects of the invention can be implemented using user interfaces, such as graphical user interfaces that can be HTML or other mark-up language based for use over the Internet or intranets or other network arrangements.

What is claimed is:

1. A method comprising:
   receiving, by a computer, in response to a computer automated survey, responses from an individual to multiple survey questions related to attitudinal factors, the individual being enrolled in a consumer directed health plan or high deductible health plan;
   receiving factual profile information about the individual, the factual profile information including one or more of income, credit score, credit balance, gender, marital status, number of dependents, arrest record, and driving record;
   predicting, by the computer, a personality trait for the individual based on responses received from the individual in response to the computer automated survey and the factual profile information about the individual, the personality trait being associated at least in part with at least one of spending attitudes of the individual and attitudes of the individual toward medical treatment;
   receiving information related to the usage of the consumer directed health plan or high deductible health plan by the individual;
   receiving information related to the income of the individual; and
   providing, based on the predicted personality trait for the individual, the information related to the usage, and the information related to the income of the individual, information about use of the consumer directed health plan or high deductible health plan to the individual, the information being different for different individuals having different predicted personality traits and different income levels;
   wherein providing the information comprises:
   for individuals having a particular personality trait, providing information related to reducing costs to the individual for medical services to individuals having an income below a threshold and providing information related to preventative healthcare to individuals having an income above the threshold.

2. The method of claim 1, wherein the method further comprises:
   determining, based on the predicted personality trait for the individual, the individual's suitability for a consumer directed health plan or high deductible health plan; and
   providing the information comprises:
   providing, to individuals determined to be suitable for a consumer directed health plan or high deductible health plan, one or more of information related to preventative healthcare and information related to reducing costs to the individual for medical services; and
   providing, to individuals determined to be unsuitable for a consumer directed health plan or high deductible health plan, one or more of information about changing the individual's type of health plan and information about appropriate use of the consumer directed health plan or high deductible health plan.

3. The method of claim 1, wherein the information about use of the consumer directed health plan or high deductible health plan comprises information related to locating a health care, provider.

4. The method of claim 1, wherein the predicted personality trait is based on a measure of financial astuteness of the individual.

5. The method of claim 1, wherein predicting the personality trait for the individual comprises predicting the personality trait for the individual based on at least one of past interaction information, demographic data, and credit bureau data.

6. The method of claim 1, wherein computer automated survey comprises 30 questions or fewer.

7. A method comprising:
   receiving, by a computer, in response to a computer automated survey, responses from an individual to multiple survey questions related to attitudinal factors, the individual being enrolled in a consumer directed health plan or high deductible health plan;
   receiving factual profile information about the individual, the factual profile information including one or more of income, credit score, credit balance gender, marital status, number of dependents, arrest record, and driving record;
   predicting, by the computer, a personality trait for the individual based on responses received from the individual in response to the computer automated survey and the factual profile information about the individual, the personality trait being associated at least in part with at least one of spending attitudes of the individual and attitudes of the individual toward medical treatment;
   receiving information related to the usage of the consumer directed health plan or high deductible health plan by the individual;
   receiving information related to the income of the individual; and
   providing, based on the predicted personality trait for the individual, the information related to the usage, and the information related to the income of the individual information about use of the consumer directed health plan or high deductible health plan to the individual, the information being different for different individuals having different predicted personality traits and different income levels;

determining, based on the predicted personality trait for the individual, the individual's suitability for a consumer directed health plan or high deductible health plan; and wherein providing the information comprises:

providing, to individuals determined to be suitable for a consumer directed health plan or high deductible health plan, one or more of information related to preventative healthcare and information related to reducing costs to the individual for medical services; and providing, to individuals determined to be unsuitable for a consumer directed health plan or high deductible health plan, one or more of information about changing the individual's type of health plan and information about appropriate use of the consumer directed health plan or high deductible health plan.

8. The method of claim 7, wherein providing the information comprises:
for individuals having a particular personality trait, providing information related to reducing costs to the individual for medical services to individuals having an income below a threshold and providing information related to preventative healthcare to individuals having an income above the threshold.

9. The method of claim 7, wherein the information about use of the consumer directed health plan or high deductible health plan comprises information related to locating a health care provider.

10. The method of claim 7, wherein the predicted personality trait is based on a measure of financial astuteness of the individual.

11. The method of claim 7, wherein predicting the personality trait for the individual comprises predicting the personality trait for the individual based on at least one of past interaction information, demographic data, and credit bureau data.

12. The method of claim 7, wherein computer automated survey comprises 30 questions or fewer.

* * * * *